United States Patent [19]
Douglas

[11] Patent Number: 5,581,014
[45] Date of Patent: Dec. 3, 1996

[54] METHOD AND APPARATUS FOR ACOUSTIC ANALYSIS OF BINARY GAS MIXTURES WITH CONTINUOUS SELF-CALIBRATION

[76] Inventor: David W. Douglas, 9323 Alden Rd., Lenexa, Kans. 66215-3038

[21] Appl. No.: 416,641

[22] Filed: Apr. 5, 1995

[51] Int. Cl.[6] .................................. G01N 29/18
[52] U.S. Cl. .................. 73/24.01; 73/611; 331/154
[58] Field of Search ............... 73/24.01, 24.05, 73/24.06, 597, 602, 611, 617; 331/65, 74, 154, 155

[56] References Cited

U.S. PATENT DOCUMENTS

| | | | |
|---|---|---|---|
| 2,978,899 | 4/1961 | Kritz | 73/24.01 |
| 3,621,453 | 11/1971 | Ringwall | 331/155 X |
| 3,848,457 | 11/1974 | Behymer | 73/24.01 |
| 3,852,724 | 12/1974 | Schwartz | 333/154 X |
| 4,255,964 | 3/1981 | Morison | 73/24.01 |
| 4,281,299 | 7/1981 | Newbold | 333/133 X |
| 5,060,506 | 10/1991 | Douglas | 73/24.01 |
| 5,060,507 | 10/1991 | Urmson et al. | 73/24.01 |

FOREIGN PATENT DOCUMENTS 3009566  9/1981  Germany ........................... 73/24.01

*Primary Examiner*—Michael Brock
*Attorney, Agent, or Firm*—Kokjer, Kircher, Bowman & Johnson

[57] ABSTRACT

A method and apparatus for acoustic analysis of binary gas mixtures. A binary gas sample is drawn into a first chamber. A known reference gas is drawn into a second chamber. Acoustic energy is simultaneously transmitted through the respective chambers. Arrival of the first acoustic wave at the receiver of the reference chamber starts a counter that isolates a selected received pulse. The time between receipt of that selected reference pulse and the very next sample pulse is monitored and is transferred to a short term memory and then returned to its initial zero condition. After a quiescent time delay, the sequence is repeated. The resulting signal may be output as data and/or activate alarms if the output does not remain between predetermined upper and lower thresholds, thereby indicating an undesirable binary gas mixture.

13 Claims, 2 Drawing Sheets

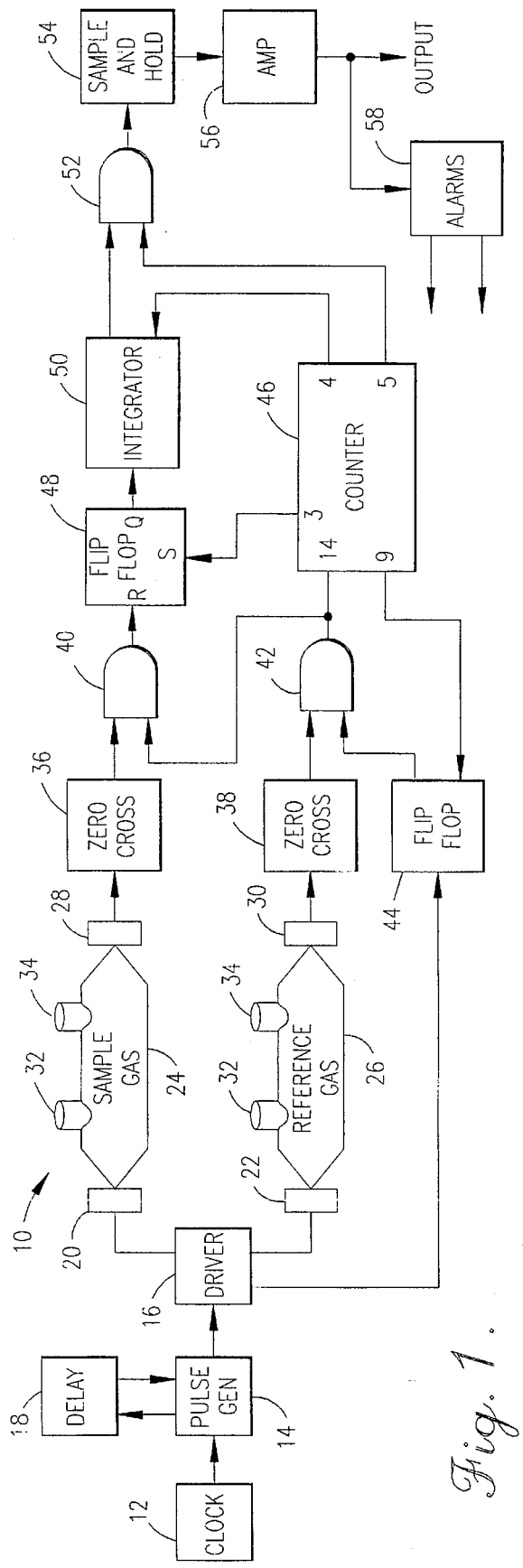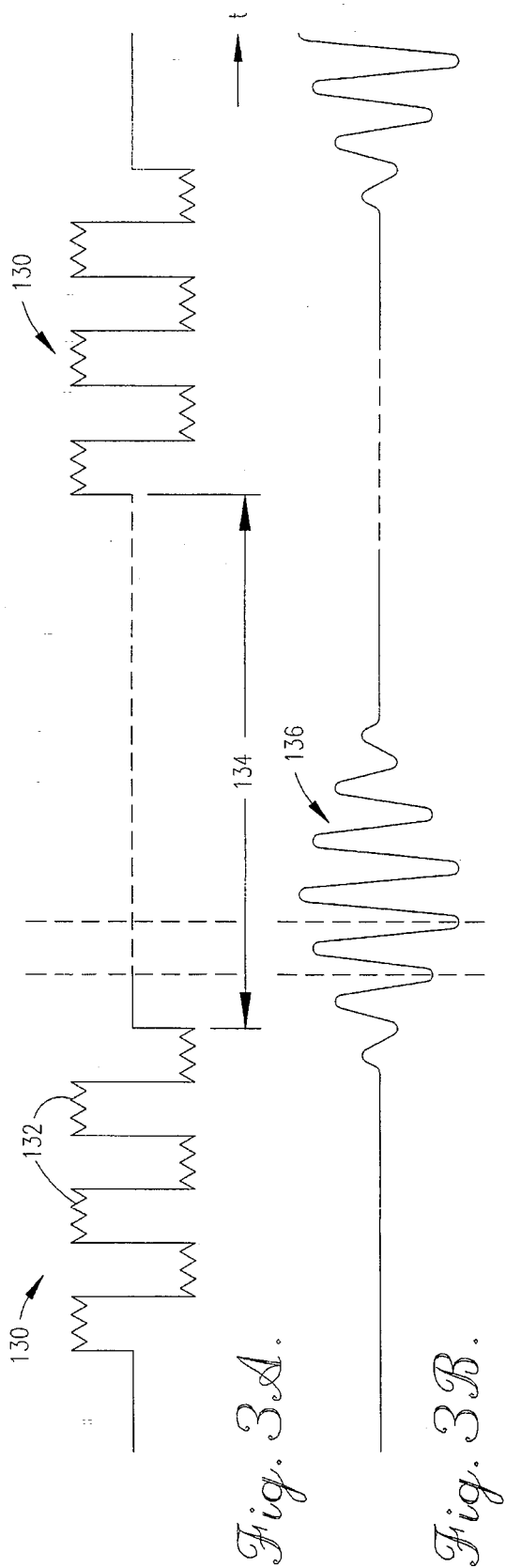

METHOD AND APPARATUS FOR ACOUSTIC ANALYSIS OF BINARY GAS MIXTURES WITH CONTINUOUS SELF-CALIBRATION

BACKGROUND OF THE INVENTION

1. Field of the Invention

The present invention relates generally to a method and apparatus for acoustically analyzing the ratios of a mixture of gases consisting essentially of two known gases. Particularly, the present invention is related to such a method and apparatus that utilizes transmission of ultrasound through each of a reference and sample gas, and that utilizes the ringing signal in the electronic receiver circuitry which receives the ultrasound signal transmitted through the reference gas, as a clock.

2. Description of the Related Art

There is a recognized need in both industry and medicine for a reasonably accurate, modestly priced, stable, continuous monitor of binary (two-gas) mixtures. Although numerous types of instruments are commercially available to perform analyses of gas mixtures, most are expensive and complex because they are designed to laboratory standards for monitoring specific gases. In many cases, the fragile nature of laboratory-designed instruments makes such monitors impractical for industrial utilization. Devices suitable for industrial use, such as an air pollution study where several gases are present, typically require complex methods of analysis, such as mass spectrometry.

One known method of monitoring binary gas mixtures is illustrated in my U.S. Pat. No. 5,060,506. U.S. Pat. No. 5,060,506 recognizes that the velocity of sound through a gas varies with the gas composition and with temperature. A gas mixture is passed through a sample tube within which ultrasound waves travel in successive bursts of pulses at the resonant frequency of a transmitter/receiver pair. Between pulse bursts is a quiescent time period having a duration long enough to dissipate transients, so that standing waves do not form. A resulting voltage, which is proportional to the transit time of the ultrasound through the gas mixture, as well as to temperature error, is first corrected for gas temperature and then is available to measure the gas composition. It can also be compared with adjustable reference voltages to trigger high and low alarms.

More specifically, U.S. Pat. No. 5,060,506 teaches transmission of a brief burst of ultrasound energy through the body of a transducer at the resonant frequency common to both the transmitter and receiver elements of the transducer. A following quiescent period is sufficiently long to allow for dissipation of unwanted excess acoustical energy. A pulse transmitted from the transmitter to the receiver is selected electronically for analysis of transit time, long before standing waves can be established. The transit time analog value is stored during the quiescent period, and then up-dated by the subsequent pulse burst.

The teachings of my U.S. Pat. No. 5,060,506 are highly useful in the analysis of binary gas mixtures and, particularly, for monitoring gas purity from oxygen concentrators for respiratory care. Although the device and method described in my U.S. Pat. No. 5,060,506 is highly useful for its intended purposes, it is subject to some zero error caused by natural non-linearities in temperature effects and mechanical temperature coefficients within the transducer assembly. Another source of error is different specific heat ratios of various gases, but this is sufficiently small that it can generally be ignored. In addition to temperature-related errors is difference in the velocity of the flowing gases, which adds to the velocity of sound. At five liters per minute maximum in oxygen concentrators, the error is small enough to be ignored, but in many industrial applications, a closer tolerance is needed than is readily available with the device of my U.S. Pat. No. 5,060,056. Avoidance of routine calibration is also a prerequisite for most industrial applications.

Since acoustic monitoring of binary gases is affected by temperature and velocity changes to the gas, the need exists for a binary gas monitoring device that continuously compensates itself for changes in temperature and flow rate, thereby preventing repeated calibration by the user. The need also exists for such a device that is inexpensive and easy to manufacture, and does not require an expensive high-frequency system clock for operation. The need further exists for such a gas monitoring device that is operable at close tolerances to monitor even slight changes in composition of a binary gas. The present invention overcomes the drawbacks of the prior art and fills the foregoing and other needs.

A particular need addressed by the present invention is in gas generation and processing. One example is in the generation of ozone for water purification, odor elimination, bleaching, etc. Air, oxygen, or a mixture of both (air can be regarded as a single gas of molecular weight 29) is fed into a corona discharge tube and some percentage of the oxygen ($O_2$) introduced is converted to ozone ($O_3$). The entering $O_2$ is the reference gas, the exiting $O_3$ the sample. Another is in membrane separation of nitrogen from air for food storage, in which oxygen is a contaminant. In these two examples, flow rates into and out of the process are equal. A third example is in monitoring the purity of a sample gas against a standard gas which may be flowing at a different rate or not flowing at all. The error that can be caused by such unequal flow rates is corrected most easily in the transducer design, which will be described below.

SUMMARY OF THE INVENTION

It is an object of the present invention to provide a method and apparatus for acoustic analysis of binary gas mixtures, including continuous automatic compensation for temperature and flow rate changes.

It is a further object of the present invention to provide a device for clocking operation of analytical sequences performed by electronic circuitry, using the ringing of an electrically excited resonant receiver.

It is also an object of the present invention to provide a device and method for acoustically analyzing binary gas mixtures, which prevents undesirable transient acoustic energy from interfering with monitoring of gas mixtures.

These and other objects are achieved by a practical and economical monitor for analyzing the concentration of gases in a gas mixture consisting of essentially two known gases. The present invention utilizes, in part, the physical phenomenon that sound waves travel at different velocities through different gases, so the principles of the invention are applicable to all binary gas mixtures of differing molecular weights.

The velocity of sound through a gas at constant temperature is approximated by $V=(e/d)^{1/2}$, where "V" is the velocity, "e" is the adiabatic elasticity, and "d" is the density. Pressure alters e and d proportionally, so pressure does not affect the velocity, a significant advantage of ultrasound technology. Taking the effect of temperature into account and assuming there are no standing waves present, the velocity is $V=(eRT/M)^{1/2}$ where "R" is the universal gas constant, "T" is the absolute (Kelvin) temperature, and "M" is the molecular weight of the gas. In a binary gas mixture, by monitoring the sound velocity and taking temperature into account, the relative concentrations are revealed. In any binary gas mixture, when a change in composition occurs, the molecular exchange between the two components is one-to-one, in accordance with Avogadro's Law. Thus, the shift in mean molecular weight, as well as in the velocity of sound, during a change in composition of the gaseous mixture, is absolutely linear. However, temperature error is not linear: the general simplified equation of $(dV/dT)=k(T)^{-3/2}$ holds.

Having set forth the foregoing general physical principles applicable to binary gas mixtures, the present invention provides a gas monitor having improved characteristics for analyzing the relative percentage of a mixture of two gases while continuously compensating itself for changes in temperature of the gases and their velocity. First and second essentially identical transducer cells serve as chambers for a reference gas and a sample gas, respectively. Each transducer cell contains an opposing ultrasound transmitter and receiver pair resonant to a corresponding frequency. The transmitters are driven at that resonant frequency with a single electrical pulse or a short burst of pulses, thereby transmitting ultrasound through the gas-containing cells.

To increase the sensitivity of the present gas monitor, a long pathway may be provided between the transmitter and receiver of each pair. To minimize attenuation of the acoustic energy when a long pathway is necessary, hoses wound in space-conserving fashion may be used as acoustic wave guides.

Because dimension prerequisites and propagation times depend upon the gases being monitored and the levels of sensitivity necessary for a given system, the timing and sequencing of the analytical steps that take place after the sound propagation cannot be easily controlled by a system clock. The principles of the present invention overcome the need for such a clock.

The gas monitor of the present invention is designed so that sound propagated through the reference gas reaches its associated receiver first. Ensuring that the sound propagated through the reference gas arrives first can be accomplished in several ways. In one embodiment, the two chambers are mechanically trimmed to the appropriate length. In another embodiment, the output signal from the receiver of the sample chamber is phase shifted to ensure that it arrives at a counter later in time than the output signal from the reference chamber.

In some applications, such as in sampling gases for purity against a known standard gas, the sample gas may flow while the standard gas may not. The resulting flow rate error can be made self-cancelling in the transducer design. In one embodiment, a valve can momentarily stop the flowing gas during periodic measurement. In another embodiment, the flowing gas pathway may be from the mechanical center to both ends of the transducer, thus cancelling the flow rate error.

In order to overcome the need for control by an external system clock, the present invention utilizes the resonant characteristics of the receiver elements for timing and sequencing. Particularly, when the driving force of a transmitter is released, its associated receiver continues to absorb the energy that has been generated, ringing at its natural resonant frequency for many subsequent cycles. This ringing provides the source of timing and sequencing for the gas monitor of the present invention.

In operation, the transmitters of each cell are simultaneously driven to emit acoustic energy. In one embodiment, a single acoustic pulse is transmitted. In another embodiment, a plurality of pulses (e.g., 3) are emitted from the transmitters. Arrival of the first acoustic wave at the receiver of the reference cell starts a counter that isolates a selected received pulse (e.g., the $n^{th}$ pulse). The time between receipt of that selected reference pulse and the very next sample pulse is monitored and integrated. The integral is transferred to a short-term memory and then returned to its initial zero condition. A quiescent time delay is initiated, and the sequence is repeated. Alarm circuitry is activated if the integral during any cycle of operation does not remain between predetermined upper and lower thresholds, thereby indicating an undesirable gas mixture.

BRIEF DESCRIPTION OF THE DRAWINGS

The objects and features of the invention noted above are explained in more detail with reference to the drawings, in which like reference numerals denote like elements, and in which:

FIG. 1 is a block diagram of the present invention;

FIGS. 3A and 3B are diagrammatic views of waveforms at various parts of the circuitry.

DETAILED DESCRIPTION OF THE INVENTION

Figure 2:
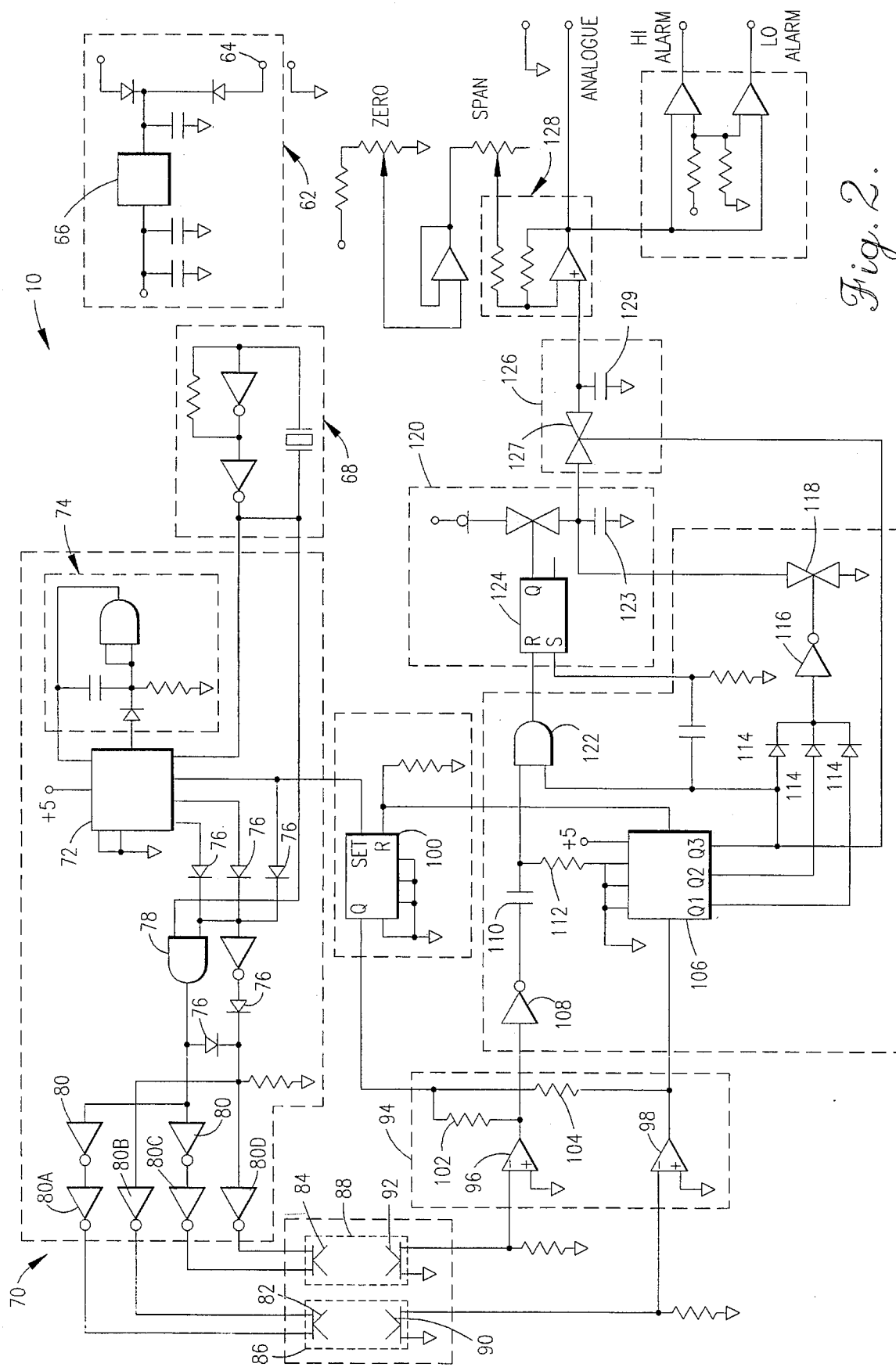
FIG. 2 is a schematic circuit diagram of the binary gas monitor of the present invention having the ability to provide a clock signal at a preselected frequency.

Referring now to the drawings in more detail and to FIG. 1 in particular, reference numeral 10 generally designates a gas monitoring device constructed in accordance with the principles of the present invention and suitable for use in monitoring the relative concentration of a gaseous mixture consisting of essentially two known gases. Gas monitoring device 10 is preferably secured within a housing (not shown).

A power supply (not shown) is a source of electrical power for gas monitoring device 10. A clock 12 is coupled with a pulse generator 14 which is in turn coupled to a driver 16. Delay circuitry, denoted generally by the block 18, is coupled with pulse generator circuitry 14, as shown.

Driver circuitry 16 is connected to transmitters 20, 22. Transmitters 20, 22 are shown in block form, and are respectively positioned at a first end of sample and reference gas chambers 24, 26. A receiver 28 (shown in block form) is positioned at a second end of sample gas chamber 24. A receiver 30 (shown in block form) is positioned at a second end of reference gas chamber 26. Sample and reference gas chambers 24, 26 each have input ports 32 through which an appropriate gas is drawn into its associated chamber 24, 26. Chambers 24, 26 also have an output port 34 through which the gas drawn through the chamber is exited.

Receivers 28, 30 are respectively connected to zero crossing detectors 36, 38, which are in turn respectively coupled with AND gates 40, 42, as shown. Driver circuitry 16 is also coupled with a first flip-flop 44. The output of flip-flop 44 is input into AND gate 42. The output of AND gate 42 serves as an input for AND gate 40, and also for counter 46. The output of AND gate 40 connects with the reset pin "R" of a second flip-flop 48, while a selected counter pin (pin 3) of counter 46 is connected with the set pin "S" of flip-flop 48. Counter 46 and flip-flop 48 are connected with integrator circuitry, denoted by block 50, as shown. Counter 46 and integrator 50 are connected through AND gate 52 to sample and hold circuitry 54. The output of sample and hold circuitry 54 is connected through an amplifier 56 and to alarm circuitry 58.

The operation of monitoring device 10 will be described in detail below in connection with FIGS. 2 and 3. With reference to FIG. 1, pulse generator 14 and driver 16 energize transmitters 20 and 22, and set flip-flop 44. As will be discussed below, transmitters 20 and 22 may be energized with a single pulse generated by the pulse generating circuitry of the present invention or, alternatively, by a plurality of pulses. Delay circuitry 18 serves to create a quiescent delay period between each period of energization. When flip-flop 44 is set, its output activates the zero crossing detectors thereby permitting a signal to pass the zero crossing detectors.

The binary gas to be monitored, called the sample gas, is drawn through sample gas chamber 24 from its inlet port 32 to its outlet port 34. A reference gas, consisting of one of the gases of the binary gas drawn through sample gas chamber 24, is drawn through reference gas chamber 26 from its inlet port 32 to its outlet port 34. Transmitters 20, 22, when excited, emit acoustic signals through their respective chambers. Receipt of the acoustic signals at transmitters 28 and 30, respectively, cause the receivers 28, 30 to oscillate (or ring).

In accordance with the principles of the present invention, a signal representative of the ringing reference receiver 30 activates counter 46. Counter 46 counts a selected number of cycles of the cyclical signal emitted from receiver 30 and, upon occurrence of the selected cycle, sets flip-flop 48. Counter 46 continues counting. Subsequently, the very first signal from sample gas receiver 28 resets flip-flop 48. The time between the selected reference pulse and the first signal from receiver 28 is integrated by integrator 50. It will be appreciated that the integral can be used to determine the ratio of the two known gases. This type of analog integrator is often called a ramp generator. The results may be output (through amp 56) and/or compared with predetermined thresholds whereupon an alarm will occur if an upper or lower threshold is exceeded.

It will be appreciated that the preferred circuit arrangement as shown and described in connection with FIG. 1 can be constructed in various manners utilizing alternative components. Accordingly, FIG. 1 shows the preferred embodiment of the present invention, a specific preferred embodiment of which is illustrated in FIG. 2.

With reference now to FIG. 2, the preferred circuitry of the present invention is described. A power supply 62 is a source of electrical power for gas monitoring device 10. Power supply 62 is preferably 5 volts DC, regulated. Power supply 62 is a conventional power supply, and may be a battery or have an AC line input, such as shown at reference numeral 64, feeding into a voltage regulator 66. Reference numeral 68 denotes a 25 KHz clock. Other frequencies for clock 68 may be utilized.

Clock 68 is coupled with transmitter driver circuitry 70. Transmitter driver circuitry 70 has a counter 72, preferably of a type such as those commercially available under part number 4017BE. Clock 68 is specifically coupled to the clock input lead of counter 72 (pin 14). A 40 millisecond delay timer 74 is coupled between output Q9 (pin 11) and RESET (pin 15) of counter 72. Five volts DC is applied to pin 16 of counter 72. Pins 8 and 13 of counter 72 are grounded. Logic circuitry is coupled to outputs Q1 (pin 2), Q2 (pin 4), and Q3 (pin 7) of counter 72. The logic circuitry includes diodes 76, an AND gate (part number 4081BE) 78, and inverters 80, all connected as shown.

The output connections of transmitter driver circuit 70 are now described. Outputs from inverters 80A and 80B are connected to a first resonant transmitter 82. Outputs from inverters 80C and 80D are connected to a second resonant transmitter 84. First resonant transmitter 82 is positioned in a first chamber 86, while second resonant transmitter 84 is positioned in a second chamber 88. A first resonant receiver 90 is positioned at the end of first chamber 86 opposite transmitter 82. A second resonant receiver 92 is positioned at the end of second chamber 88 opposite second transmitter 84. Chambers 86, 88 are preferably cylindrical plastic tubes. In accordance with the principles of the present invention, chambers 86, 88 have ports therein (See FIG. 1) for receiving a flow of gas therethrough. Specifically, first chamber 86 serves as a reference chamber for receiving a known reference gas. Second chamber 88 serves as a sample chamber for receiving a sample of gas consisting essentially of two known gases of some proportion, one of which gases is the reference gas.

The respective outputs of resonant receivers 90, 92 are connected through a pair of zero crossing detectors, denoted generally by reference numeral 94. Each zero crossing detector 96, 98 of pair 94 is preferably of a type available under part number TLC372CP. Specifically, the output of resonant receiver 90 in the reference gas chamber 86 is coupled to the negative input of detector 98 and the output of resonant receiver 92 in the sample gas chamber is coupled to the negative input of detector 96, as shown.

Output Q3 of counter 72 is also coupled to the SET pin 9 of flip flop 100. Flip flop 100 is preferably a device such as is commercially available under part number 9027BE. Output Q (pin 15) of flip flop 100 is connected through resistors 102, 104 to the output of detectors 96, 98, respectively, of the zero crossing detector pair 94. The connection of the RESET pin 12 of flip flop 100 is described below. All other pins of flip flop 100 are grounded.

The outputs from zero crossing detector pair 94 are coupled with counter 106. Counter 106 is preferably of a type such as is commercially available under part number 9017BE. Pins 8, 13, and 15 of counter 106 are connected between ground and the output of op amp 96, through inverter 108, capacitor 110, and resistor 112. A positive five volts DC is applied to pin 16 of counter 106. The output of detector 98, and hence the output of resonant receiver 90 in reference chamber 86, is connected to the clock input (pin 14) of counter 106. Output Q0 of counter 106 (pin 3) is connected to the RESET pin 12 of flip flop 100.

Three selected outputs of counter 106, shown as Q1, Q2, and Q3 for reference purposes, are connected as shown. Particularly, each output Q1–Q3 of counter 106 is coupled through a diode 114 to a return to zero circuit comprised of inverter 116 and switch 118, the latter of which is preferably of a type such as is commercially available under part number 4066BCP. The output of the return to zero circuit is connected with an integrator, denoted generally by reference numeral 120. A selected output of counter 106 (Q3 as illustrated) also couples through gate 122 to integrator 120 and to a transfer circuit 126, which is in turn coupled with sample and hold circuit 128. Integrator 120 includes a flip flop 124, connected as shown. Flip flop 124 is preferably of a type as is commercially available under part number 4027BE. Coupled with the sample and hold circuit 128 are ZERO and SPAN controls, as shown.

It will be appreciated by those skilled in the art that numerous variations of the foregoing circuit are possible without departing from the spirit and scope of the present invention. For example, various components could be substituted for those shown for illustrative purposes. Furthermore, the logic circuitry of the transmitter driver circuit 72, the components and connections associated with circuits 120, 126, 128, the ALARMS, and the ZERO and SPAN controls, and/or the named pin connections could all be easily varied by one skilled in the art without departing from the principles of the present invention. Display devices could be connected to device 10 for visual monitoring purposes. The output signal can also be used as a control signal in a closed-loop servo controller.

In operation, gas monitoring device 10, powered by power supply 62, is operable for determining the proportion of gases in a gaseous mixture consisting of essentially two known gases. A sample of a gaseous mixture to be monitored, consisting of essentially two known gases, and therefore referred to as a binary gas, is drawn into sample chamber 88. Simultaneously, a reference gas, usually consisting of one of the two known gases in the sample gas, is directed through reference chamber 86.

Transmitter driver circuit 70 applies an excitation signal to the resonant reference transmitter 82 and the resonant sample transmitter 84. Specifically, the excitation signal is comprised of a selected number of excitation pulses. In one preferred embodiment, each excitation signal is made up of a plurality excitation pulses, as shown diagrammatically in FIG. 3A where a preferred three pulses are shown. Each series of the selected number of pulses (e.g., three pulses) is referred to as a burst of pulses. The transmitter driver circuit 70, and particularly timer 74, operate to cause a quiescent period between each burst of pulses, as illustrated in FIG. 3A. Preferably, each pulse burst includes three 25 KHz pulses having a total duration of 720 microseconds. The quiescent delay period is preferably 20–40 milliseconds, which is sufficient time to allow dissipation of undesirable transient energy in the chambers 86, 88. The logic circuitry of transmitter driver circuit 70 is arranged to reverse the polarity each half cycle of the selected number of half cycles (e.g., 3 half cycles). As a result, the transmitters 82, 84 actually "see" a bi-polar square wave with no potential applied during the quiescent period.

The excitation signal for exciting transmitters 82, 84 may be comprised of a single excitation pulse followed by a quiescent period. It will be appreciated that various pulse generating devices are available, and that substitutions may be made. For instance, a one-shot multivibrator may be utilized to generate a single excitation pulse.

Because of the connection between counter 106 and flip flop 100, the transmitted excitation pulses also set flip flop 100, thereby placing the output of flip flop 100 in a high state, and thus providing power to both zero crossing detectors 96, 98 in the pair 94.

Receipt of the excitation pulses by transmitters 82, 84 cause the transmitters to emit sound waves (ultrasonic) at a selected resonant frequency. Each transmitter 82, 84 has the same resonant frequency (preferably 25 kHz). The sound waves emitted by reference transmitter 82 are transmitted through the reference gas in the reference chamber and received by receiver 90. The sound waves emitted by sample transmitter 84 are transmitted through the sample gas in the sample chamber and received by receiver 92. It should be understood that the velocity at which each sound wave is transmitted from its source transmitter to its associated receiver is a function of the mean molecular weight of the gas through which the sound wave is being transmitted, the temperature of the gas, and the velocity at which the gas is flowing. In applications where the flow rate of the gases may be problematic and give rise to error, it is preferred to introduce the gas flow into the chambers 86, 88 at a center location and collect it at each end of the respective chambers. In this way, any error caused by the gas flow rate cancels itself. As previously mentioned, the length of the chambers 86, 88 may be increased to increase the sensitivity of device 10. To conserve space, chambers 86, 88 may comprise wave guides wound in space conserving fashion.

Upon receipt of a sound wave by a resonant receiver 90, 92, the receiver begins resonating (or ringing), as illustrated by the signal shown in FIG. 3B. As discussed in detail below, device 10 is designed so that reference receiver 90 receives a sound wave signal before sample signal 92 receives a sound wave. The ringing output signal at receiver 90 is transmitted through its associated zero crossing detector to counter 106. Importantly, receiver 90 continues to ring even after the excitation signal applied to transmitter 82 has been ceased. The output of zero crossing detector 98 acts as a clock for counter 106. Counter 106 is initiated upon receipt of the first reference cell wave output from zero crossing detector 98. As mentioned, the transit time of acoustic energy through gases is affected by temperature in a non-linear fashion. However, in accordance with the principles of the present invention, the first arrived pulse through the reference gas starts the measuring process, and thus constitutes zero reference. Accordingly, temperature influences transit time of the acoustical energy in the sample chamber equally. Having thereby compensated for temperature changes, and by cancelling any gas flow rate differences as discussed above by introducing gas flow at the center of the chambers 86, 88, the only remaining variable affecting transit time of acoustic energy through the sample gas is mean molecular weight, and thus the ratio of the gas components.

The counter 106, once initiated, then identifies a selected pulse, as shown diagrammatically in FIG. 3B. Preferably, counter 106, once initiated by receipt of the first pulse of the reference cell output wave, selects the third such pulse and, upon receipt of the selected third pulse, sets flip flop 124. FIG. 3 diagrammatically illustrates the waveform phenomena utilized by the present invention. FIG. 3A represents a pulse burst 130 of three pulses for energizing the transmitters 82, 84. Each pulse burst 130, which may contain one or more pulses 132, is followed by a quiescent period 134 controlled by delay timer 74, which is in turn followed by a subsequent pulse burst 130.

FIG. 3B illustrates the oscillation signal 136 of an excited receiver 90, 92 upon its receipt of an acoustic signal. Particularly, FIG. 3B illustrates the manner in which receivers 90, 92 continue to oscillate after excitation of transmitters 82, 84, respectively, has ceased. As shown, oscillation of receivers 90, 92 has subsided prior to the next subsequent pulse burst 130. Also illustrated (by the dashed vertical lines) is a pulse selected from the output of reference receiver 90 in accordance with the principles of timing of the present invention. As shown, the third received pulse is selected, but it should be understood that other received pulses may be utilized.

It should be understood that, if counter 106 fails to detect the first pulse output from zero detector 98 (perhaps because of insufficient magnitude for detection by counter 106), then counter 106 will be initiated upon the next pulse of sufficient magnitude for detection and, once activated, will identify the selected pulse based upon the pulse that actually activated the counter 106. In other words, if counter 106 fails to detect the first pulse, but is activated by the next pulse, the counter 106 would select and identify the fourth pulse (e.g., three pulses from activation in the preferred embodiment) to set the flip flop 124.

Once activated, counter 106 goes through adequate counts and then resets to Q0, at the same time resetting flip flop 100 and preparing for the next burst of pulses (e.g., the next cycle). Counter outputs Q1, Q2, and Q3 arm or make ready the integrator 120 by un-shorting switch 118 when the first reference signal is received at counter 106. The Q signal sets flip flop 124, which turns on switch 125 to start the integration process.

Receipt by counter 106 of the very next detected sample pulse, from the output of zero crossing detector 96, resets flip flop 124, to thereby cease the integration process. Receipt of this very next sample pulse furthermore resets flip flop 124 and opens switch 118. The flip flop output, now integrated into a D.C. analog voltage, is transferred to a short-term memory at the sample and hold stage (e.g., sample and hold circuitry 128). Specifically, the voltage on capacitor 123 remains constant during Q3, when switch 127 transfers the voltage to capacitor 129 and then shuts off. The voltage on capacitor 129 is the result of the integration process, and hence indicative of the ratio of the two known gases in the gas sample. This value is compared, at the ANALOGUE input, with selected values. If the ratio does not fall within predetermined threshold limits, an appropriate output, such as an alarm, is made. At Q0 the sequence is complete, and the analog value is held on the output of sample and hold circuit 128 for possible updating on the next cycle some 40 milliseconds later.

As previously mentioned, it is important to assure that the set signal arrives at flip flop 124 before arrival of the reset signal; otherwise, the flip flop output is undefined. In one embodiment, the transducer path length of the reference chamber 86 is made shorter than the path length of the sample chamber 88. If this mechanical offset is small, it would clearly satisfy the condition in which the sample gas grows heavier than the reference gas. However, as the sample gas grows lighter, the analog signal output progresses toward zero and, at the zero point, reverses the triggering sequence to the flip flop 124, thereby producing undefined results. Accordingly, although it is a contemplated principle of the present invention to provide a reference chamber that is shorter (by a predetermined length) than the sample chamber, such an embodiment should not be used in certain limited situations. Furthermore, in such an embodiment, inverting buffer 108 is removed.

In order to overcome the drawbacks of mechanically offset transducer path lengths, another embodiment of the present invention is to provide phase shifts between the two receiver output signals. This is accomplished by the single inverting buffer 108 positioned between detector 96 and capacitor 110. In such an embodiment, the analog output from the integrator 170 will be one-half of its maximum value when the reference gas and the sample gas are identical. This somewhat large offset is easy to cancel electronically. In other words, if the desired integrator output is zero under ideal conditions (e.g., no contamination in the output gas), then the final analog integrator output signal is free to go positive if the contaminant is heavier than the reference gas, and vice versa. Accordingly, this second embodiment using a phase shifting of receiver output signals provides a simple solution without risk of the integrator entering undefined zones.

The zero control provides for electronic cancellation of any offset and, particularly, of the deliberate mechanical transducer length offset described above. The span control provides for conventional amplitude calibration.

It will be appreciated by those skilled in the art that various binary gas mixtures may be analyzed with the present invention. For example, an application may require monitoring of membrane-produced nitrogen for oxygen contamination. In such an application, the reference chamber 86 contains pure nitrogen, while the sample chamber 88 contains the produced nitrogen (comprised essentially of nitrogen and oxygen). Of course, various gas mixtures may be monitored by device 10 (e.g., including oxygen, air, nitrogen, carbon dioxide, ozone, etc.), and the present invention is not limited to monitoring specific gases.

The binary gas monitoring device and method provides continuous real-time analysis of the relative percentage of gases in a mixture of essentially two known gases. The utilization of the ringing that inherently follows excitation in a resonant system is highly useful for clocking the analytical sequence and operation of the present invention. The utilization of a first received and detected electrical pulse for starting an analytical sequence, followed by clocking with inherent ringing in a resonant receiver, is particularly advantageous in combination with the pulse-burst generator described herein, wherein provision of a sufficient quiescent time period assures that any transient energy will sufficiently dissipate.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

What is claimed is:

1. An apparatus for monitoring the content of a gas sample consisting essentially of two known gases, said apparatus comprising:

a sample chamber for receiving the gas sample;

a reference chamber for receiving a known reference gas;

a first resonant transmitter, in said reference chamber, excitable at a predetermined resonant frequency and operable when excited to transmit sound waves through the reference gas in said reference chamber;

a second resonant transmitter, in said sample chamber, excitable at said predetermined resonant frequency of said first transmitter, said second resonant transmitter operable when excited to transmit sound waves through the sample gas in said sample chamber;

a driver for exciting each said transmitter with an excitation signal comprised of a preselected number of excitation pulses;

a first resonant receiver, in said reference chamber, for receiving the sound waves transmitted by said first resonant transmitter, said first resonant receiver being resonant at said predetermined resonant frequency, wherein said first resonant receiver generates an output signal when said first resonant receiver receives each said sound wave transmitted by said first resonant transmitter;

a second resonant receiver, in said sample chamber, for receiving the sound waves transmitted by said second resonant transmitter, said second receiver being resonant at said predetermined frequency, wherein said second resonant receiver generates an output signal when said second resonant receiver receives each said sound wave transmitted by said second resonant transmitter; and means for using said receiver output signals to generate an electrical signal indicative of the ratio of the two known gases in the gas sample, wherein said using means requires input of a clock signal to be operable, and wherein said clock signal comprises said output of said first resonant receiver.

2. The apparatus as set forth in claim 1, wherein said means for using said receiver output signals to generate an electrical signal indicative of the ratio of the two known gases in the gas sample comprises:

means for determining the difference in transit times of a sound wave transmitted through said reference gas in said reference chamber and a sound wave transmitted through said sample gas in said sample chamber.

3. The apparatus as set forth in claim 2, wherein said determining means generates an output signal indicative of said difference in transit times, said means for using said receiver output signals further comprising an integrator for integrating said output signal indicative of said difference in transit times to determine the ratio of the two known gases in the gas sample.

4. An apparatus for monitoring the content of a gas sample consisting essentially of two known gases, said apparatus comprising:

a sample chamber for receiving the gas sample;

a reference chamber for receiving a known reference gas;

a first resonant transmitter, in said reference chamber, excitable at a predetermined resonant frequency and operable when excited to transmit sound waves through the reference gas in said reference chamber;

a second resonant transmitter, in said sample chamber, excitable at said predetermined resonant frequency of said first transmitter, said second resonant transmitter operable when excited to transmit sound waves through the sample gas in said sample chamber;

a driver for exciting each said transmitter with an excitation signal;

a first resonant receiver, in said reference chamber, for receiving the sound waves transmitted by said first resonant transmitter, said first resonant receiver being resonant at said predetermined resonant frequency, wherein said first resonant receiver generates an output signal when said first resonant receiver receives each said sound wave transmitted by said first resonant transmitter;

a second resonant receiver, in said sample chamber, for receiving the sound waves transmitted by said second resonant transmitter, said second receiver being resonant at said predetermined frequency, wherein said second resonant receiver generates an output signal when said second resonant receiver receives each said sound wave transmitted by said second resonant transmitter; and means for using said receiver output signals to generate an electrical signal indicative of the ratio of the two known gases in the gas sample, wherein said means for using said receiver output signals uses said output signal from one of said receivers as a clock signal.

5. The apparatus as set forth in claim 4 further, wherein said clock signal comprises said output signal of said first resonant receiver.

6. The apparatus as set forth in claim 5, wherein said driver excites said transmitters with a preselected number of excitation pulses in successive bursts of such pulses, the initial said pulse of each burst of pulses being separated from the final pulse in the immediately preceding burst by a quiescent time period of sufficient duration to allow dissipation of any transient effect that may have existed as a result of said immediately preceding burst, thereby suppressing standing waves in each said chamber.

7. The apparatus as set forth in claim 6, wherein said means for using said receiver output signals to generate an electrical signal indicative of the ratio of the two known gases in the gas sample comprises:

means for determining the difference in transit times of a sound wave transmitted through said reference gas in said reference chamber and a sound wave transmitted through said sample gas in said sample chamber.

8. The apparatus as set forth in claim 7, wherein said determining means generates an output signal indicative of said difference in transit times, said means for using said receiver output signal further comprising an integrator for integrating said output signal indicative of said difference in transit times to determine the ratio of the two known gases in the gas sample.

9. An apparatus for providing a clock signal at a preselected frequency to a component in an electrical circuit, said component having a lead for receiving a clock signal, said apparatus comprising:

a resonant transmitter excitable at a preselected resonant frequency and operable when excited to transmit sound waves;

a driver for exciting said resonant transmitter at said preselected resonant frequency, wherein said driver generates an excitation signal having a plurality of successive bursts, each said burst including a preselected number of excitation pulses at said resonant frequency, the initial pulse in each burst being separated from the final pulse in the immediately preceding burst by a quiescent time period of sufficient duration to allow dissipation of any transient effect that may have existed as a result of said immediately preceding burst; and a resonant receiver operable to receive the sound waves transmitted from said resonant transmitter, said receiver being resonant at said preselected frequency, said resonant receiver having an output coupled with said lead of said component, wherein said receiver develops an alternating output signal at said resonant frequency responsive to said sound waves, and wherein said clock signal for said component comprises said output signal of said resonant receiver.

10. The apparatus as set forth in claim 9 further comprising a zero crossing detector coupled between said output of said resonant receiver and said lead of said component.

11. A method for monitoring the content of a binary gas sample in a monitoring device having a sample chamber for receiving a binary gas sample to be monitored, a reference chamber for receiving a known reference gas, a first resonant receiver in said reference chamber, and a second resonant receiver in said sample chamber, said method comprising:

transmitting sound waves a selected distance through the sample gas in the sample chamber and the reference gas in the reference chamber, whereupon said receivers oscillate upon receipt of a sound wave;

monitoring the difference in the duration of time it takes said sound waves to transmit said selected distance through said sample gas and said reference gas;

using the oscillation of at least one of said receivers as a timing signal in said monitoring step.

12. The method as set forth in claim 11 further including the step of integrating said difference in the duration of time it takes said sound waves to transmit said selected distance through said sample gas and said reference gas, whereby the resulting integral is indicative of the ratio of gases is said binary gas.

13. The method as set forth in claim 12 further including the step of comparing said integral with a preselected value indicative of a selected threshold ratio of gases in said binary gas.

* * * * *